US012569599B2

(12) United States Patent
Kopperschmidt et al.

(10) Patent No.: US 12,569,599 B2
(45) Date of Patent: Mar. 10, 2026

(54) CONTROL DEVICE FOR A BLOOD TREATMENT APPARATUS, BLOOD TREATMENT APPARATUS, SYSTEM AND METHOD

(71) Applicant: Fresenius Medical Care Deutschland GmbH, Bad Homburg (DE)

(72) Inventors: Pascal Kopperschmidt, Bad Homburg (DE); Stefan Konrad Marterstock, Bad Homburg (DE); Martin Urban, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 664 days.

(21) Appl. No.: 17/951,746

(22) Filed: Sep. 23, 2022

(65) Prior Publication Data

US 2023/0145918 A1     May 11, 2023

(30) Foreign Application Priority Data

Nov. 9, 2021   (DE) .......................... 102021129072.4

(51) Int. Cl.
*A61M 1/14* (2006.01)
*A61M 1/34* (2006.01)
(52) U.S. Cl.
CPC ................ *A61M 1/14* (2013.01); *A61M 1/34* (2013.01); *A61M 2205/50* (2013.01)

(58) Field of Classification Search
CPC ...... A61M 1/14; A61M 1/34; A61M 2205/50; G16H 20/17; G16H 40/60
See application file for complete search history.

(56) References Cited

U.S. PATENT DOCUMENTS

| | | | |
|---|---|---|---|
| 2005/0055242 A1* | 3/2005 | Bello ..................... | G16H 20/17 |
| | | | 705/2 |
| 2012/0277722 A1* | 11/2012 | Gerber ................ | A61M 1/3403 |
| | | | 604/503 |
| 2013/0191513 A1* | 7/2013 | Kamen ................... | H04L 67/02 |
| | | | 709/219 |
| 2013/0317850 A1 | 11/2013 | Bene et al. | |
| 2021/0046235 A1 | 2/2021 | Klewinghaus | |

* cited by examiner

*Primary Examiner* — Dirk R Bass
(74) *Attorney, Agent, or Firm* — Leydig, Voit & Mayer, Ltd.

(57) ABSTRACT
A control device for a blood treatment apparatus, such as a hemodialysis machine, is programmed to be in signal communication with a data storage for transfer of first data. In addition, the control device is programmed to control or regulate the blood treatment apparatus based on a plurality of sequences included in the first data, after the first data has been transmitted from the data storage to the control device. Further, the control device is programmed to be in signal communication with a central unit. The signal communication serves for receiving second data from the central unit. The control device is further programmed to associate the received second data, according to a predetermined rule, with the first data and to load it from the data storage and to control or regulate the operation of the blood treatment apparatus based on this data.

17 Claims, 4 Drawing Sheets

CONTROL DEVICE FOR A BLOOD TREATMENT APPARATUS, BLOOD TREATMENT APPARATUS, SYSTEM AND METHOD

CROSS-REFERENCE TO RELATED APPLICATION

Priority is claimed to German Patent Application No. DE 102021129072.4, filed on Nov. 9, 2021, the entire disclosure of which is hereby incorporated by reference herein.

TECHNICAL FIELD

The present invention relates to a control device, a blood treatment apparatus, a system, a method, a digital storage medium, a computer program product, and a computer program.

BACKGROUND

Advancing digital networking results in new opportunities and challenges with regard to software development and software deployment, especially in medical technology.

End devices, such as dialysis machines, are now highly integrated systems that should and can operate autonomously. An often existing network connection is usually used to exchange status data, for example with a monitoring program, or to implement firmware updates.

Since the interface between the end device and the local or global network is subject to increasingly stricter regulations and requirements, including those from the field of cybersecurity, special efforts are being made to keep attack surfaces or attack vectors of the end device as small as possible. For example, it is common for security-critical end devices, such as dialysis machines, to disconnect from the network during critical operation or only send data but not receive any themselves, in order to keep the possibility of manipulation as low as possible.

Cloud computing makes it possible to provide, on demand, —usually via the Internet and independent of devices—shared computer resources as services, for instance as servers, data storage or applications, promptly and with little effort. The offer and use of these computer resources is defined and usually takes place via an application programming interface (API) or via a website or app. The API is usually a set of commands, functions, protocols and objects that programmers may use to create software or interact with an external system, while the website or app, which may likewise be accessed from an external system, may provide applications for an (end) user to use them without further programming knowledge.

In this, services, which are available unilaterally and without human interaction, can be provided, on demand, in the cloud and can be called up for "self-service", so to speak, by an external system (keyword: on-demand self-service).

In addition, services may be accessed via a network with standard mechanisms, in particular using end devices such as smartphones, tablets, notebooks or workstations (keyword: broad network access).

Furthermore, computer resources may be pooled to serve multiple users as needed (keyword: resource pooling).

Services may be provided and released elastically in order to scale up and down as needed, in some cases automatically. From the user's point of view, the available computer resources may then appear unlimited and services may be modified or adapted in any way at any time (keyword: rapid elasticity).

Cloud computing also makes it possible to control and optimize computer resources on the basis of measurable figures that are collected depending on the respective performance, such as memory, bandwidth or active user accounts (keyword: measured service).

In edge computing, computer applications, data and services are moved away from central nodes, i.e. to the network periphery. For example, calculations are thereby performed decentrally, where the data actually originates or is collected and/or is required, with the aim of being able to work in a resource-saving manner and to prevent time delays caused by data transmission over a physical distance, i.e. to shorten response times.

In this, edge computing makes less demands on the bandwidth of the network connection used, together with cost savings due to lower data volumes and to the lower real-time demand on the network connection.

In both cloud computing and edge computing, a so-called remote procedure call may be implemented via a software, which makes it possible to call up system-remote functions, which are then executed on the remote software system. The result of such functions may then be transmitted back to the calling system.

SUMMARY

In an exemplary embodiment, the present invention provides a system. The system includes: a blood treatment apparatus configured to provide a blood treatment session; and a control device configured to: receive first data from a data storage; after receiving the first data from the data storage, control or regulate the blood treatment apparatus based on a plurality of sequences of control or regulating commands contained in the first data; receive second data from an external entity external relative to the blood treatment apparatus; associate the first data with the second data according to predefined rules; and load, based on the second data, the first data associated with the second data from the data storage and, based thereon, determine or generate treatment data for controlling operation of the blood treatment apparatus.

In a further exemplary embodiment, the external entity is part of a cloud or a network.

In a further exemplary embodiment, the first data, the second data and/or the treatment data comprises scripts, series of scripts, encodings regarding which scripts are to be executed, information regarding how long a script is to be executed, applications, instruction lists, recipes, parameters with which scripts are to be executed, and/or status information.

In a further exemplary embodiment, the control device is configured to control the blood treatment apparatus based on standard control data from the data storage, which is neither the first data nor the second data.

In a further exemplary embodiment, no association of first data with second data, or vice versa, is required for controlling the blood treatment apparatus based on the standard control data.

In a further exemplary embodiment, the device comprises a user interface configured to: enable a user to control, regulate, or prompt the blood treatment apparatus to be regulated or controlled; or enable a user to intervene in the control or regulation of the blood treatment apparatus.

In a further exemplary embodiment, the control device is further configured to: request or receive update data from the external entity for updating the first data and/or the standard control data stored in the data storage; and update the stored first data and/or the stored standard control data using the update data.

In a further exemplary embodiment, the control device is further configured to: request the update data from the external entity; or receive and accept the update data according to predetermined criteria.

In a further exemplary embodiment, the update data comprises a command or routine for activating or unlocking data.

In a further exemplary embodiment, the update data comprises a command for providing additional data for use in a treatment session without connection to the external entity.

In a further exemplary embodiment, the control device is further configured to: check plausibility of the first data or the second data for control of the blood treatment device before using the first data or the second data for controlling the blood treatment device; and/or check admissibility of the first data or the second data by using trigger elements.

In a further exemplary embodiment, the control device is further configured to: request new first data from the data storage and new second data from the external entity based on the plausibility check or the check for admissibility having a negative result.

In a further exemplary embodiment, the blood treatment apparatus comprises the control device.

In a further exemplary embodiment, the blood treatment apparatus is connected to the control device.

In a further exemplary embodiment, the blood treatment apparatus comprises a dialysis apparatus, a hemodialysis apparatus, a hemofiltration apparatus, or a hemodiafiltration apparatus.

In another exemplary embodiment, the present invention provides a method for controlling a blood treatment apparatus. The method includes: receiving, by a control device, first data from a data storage; after receiving the first data from the data storage, controlling or regulating, by the control device, the blood treatment apparatus based on a plurality of sequences of control or regulating commands contained in the first data; receiving, by the control device, second data from an external entity external relative to the blood treatment apparatus; associating, by the control device, the first data with the second data according to predefined rules; and loading, by the control device, based on the second data, the first data associated with the second data from the data storage and, based thereon, determining or generating, by the control device, treatment data for controlling operation of the blood treatment apparatus.

In yet another exemplary embodiment, the present invention provides a non-transitory computer-readable medium having processor-executable instructions stored thereon for controlling a blood treatment apparatus. The processor-executable instructions, when executed, facilitating performance of the following: receiving first data from a data storage; after receiving the first data from the data storage, controlling or regulating the blood treatment apparatus based on a plurality of sequences of control or regulating commands contained in the first data; receiving second data from an external entity external relative to the blood treatment apparatus; associating the first data with the second data according to predefined rules; and loading, based on the second data, the first data associated with the second data from the data storage and, based thereon, determining or generating treatment data for controlling operation of the blood treatment apparatus.

BRIEF DESCRIPTION OF THE DRAWINGS

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
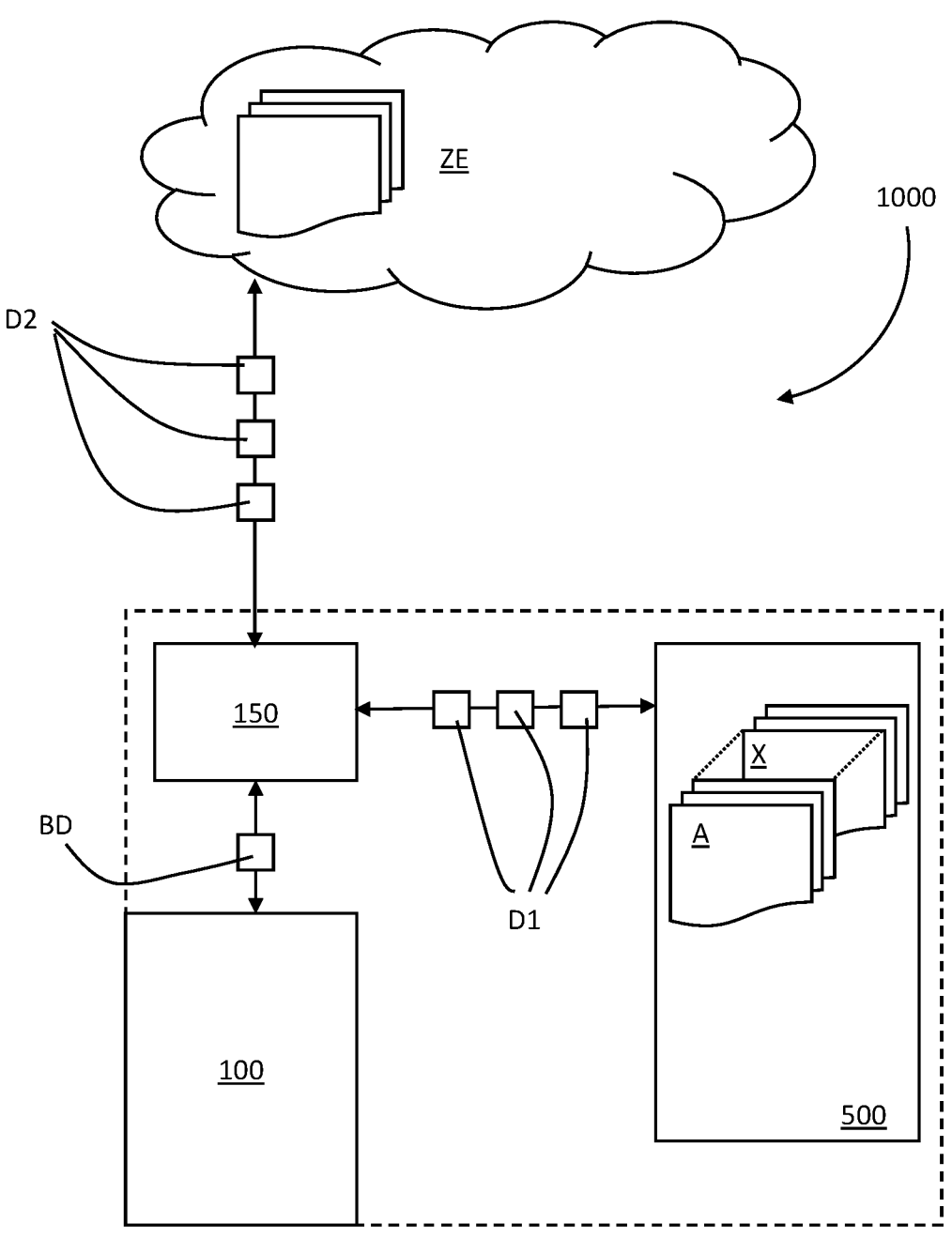
FIG. 1 shows, schematically simplified, a control device according to the present invention for a blood treatment apparatus in a system according to the present invention, in an exemplary embodiment.

In an embodiment, the present invention provides a further control device for a blood treatment apparatus.

In further embodiments, the present invention provides a blood treatment apparatus, a system and a method for controlling a blood treatment apparatus.

A control device for a blood treatment apparatus is provided by the present invention. The control device is in signal communication and/or operative communication with actuators and components of the blood treatment apparatus, such as pumps, valves, sensors, etc., for controlling or regulating the blood treatment or the blood treatment apparatus.

The control device according to the present invention is programmed, or prepared, to be in signal communication with a data storage for the unidirectional or bidirectional transfer of first data. In this, at least during operation of the control device, the data storage may be a data storage of the control device or a data storage of the blood treatment apparatus and/or may be, or prepared to be, in signal communication with the respective devices.

The control device is further programmed to control or regulate the blood treatment apparatus. This control or regulation is based on a plurality of sequences of control or regulation commands contained in the first data after the first data has been transmitted to the control device from the data storage.

Further, the control device is programmed, or provided, to be in signal communication with a unit that is not present on or in the blood treatment apparatus, i.e. to a central—herein also referred as external—unit, e.g. a cloud or a network. This signal communication serves, or is provided for, the unidirectional or bidirectional transfer of second data, which is not the first data, and in particular for receiving the second data from the central unit.

The control device is further programmed to associate first data to the—once received—second data according to predefined rules, e.g. on the basis of associations which can be derived from a stored table and/or database. This association may take place, for example, in the data storage. The control device is also programmed to load this first data, which is associated to the second data, from the data storage and/or to determine or generate from it further data, referred to herein as treatment data. In this, the second data may contain or encompass that first data may also be associated more than once, if necessary. The control device is further programmed to control or regulate the operation of the blood treatment apparatus in a current or upcoming, e.g. planned, blood treatment session by the determined or generated treatment data, or based thereon.

The first data may include scripts, with the use of which the blood treatment apparatus may treat, or a blood treatment session, or parts thereof, may proceed or run or take place. In this, it may be provided that a complete blood treatment session utilizes several such scripts which have to be processed by the blood treatment apparatus.

The second data is data that is received from the central unit with regard to the upcoming or planned, concrete treatment session, i.e. it is not present in, or not loaded from, a data storage of the blood treatment apparatus. Said second data may be, for example, sequences of scripts, parameters which are to be used with the scripts, etc.

The treatment data may include scripts, program sections or the like, by which a blood treatment apparatus may carry out a blood treatment. The treatment data is based, for example, on a correct sequence of first data (scripts), which was determined or generated based on the information from the second data and supplemented, for example, with the appropriate parameters in order to carry out treatment using the blood treatment apparatus.

According to the present invention, a blood treatment apparatus comprises, or is connected to, a control device according to the present invention and a data storage device.

In a further embodiment of the present invention, a system consists of or comprises a blood treatment apparatus according to the present invention and the central unit ZE as defined herein.

In an further embodiment, the present invention provides a method for controlling a blood treatment apparatus.

The method may include the step of providing a system according to the present invention.

Receiving second data from an external or central unit not present on or in the blood treatment apparatus, e.g. a cloud or a network, is encompassed as a further step in the method according to the present invention. For this purpose, a receiving device may be provided, which may be part of the blood treatment apparatus or of its control device.

As a further step, the method encompasses associating first data with the received second data according to predetermined rules, for example read out from a table and/or database or the like. For this purpose, an associating device may be provided, which may be part of the blood treatment apparatus or of its control device.

Transferring the first data from a data storage which is preferably present in or on the blood treatment apparatus is also encompassed by the method as a further step. For this purpose, a transfer device may be provided, which may be part of the blood treatment apparatus or of its control device.

The method further comprises controlling or regulating the operation of the blood treatment apparatus in an ongoing or upcoming, e.g. planned, blood treatment session by the associated first data, after the first data has been determined, by the control device, as control data or treatment data for the blood treatment apparatus on the basis of the second data and the association made to the first data.

A digital, particularly non-volatile storage medium, according to the present invention, particularly in the form of a machine readable carrier, particularly in the form of a diskette, CD, DVD, erasable programmable read-only memory (EPROM), ferroelectric random access memory (FRAM), or solid state drive (SSD), particularly with electronically or optically readable control signals, can interact with a programmable computer system, such that a conventional control device of a blood treatment apparatus is programmed or reprogrammed to be a control device according to the present invention.

A computer program product according to the present invention, comprises program code stored on a machine-readable program carrier, by which a control device of a blood treatment apparatus is programmed or reprogrammed to be a control device according to the present invention when the computer program product is running on a computer. A computer program product may be understood according to the present invention as e.g. a computer program stored on a carrier, an embedded system being a comprehensive system with a computer program (e.g., an electronic device with a computer program), a network of computer implemented computer programs (e.g. client/server-system, a cloud computing system etc.), or a computer on which a computer program is loaded, runs, is stored, is being executed or developed.

The term "machine readable carrier" as it is used herein, refers in certain embodiments of the present invention to a carrier, which contains data or information interpretable by software and/or hardware. The carrier may be a data carrier, such as a diskette, a CD, DVD, a Universal Serial Bus (USB) stick, a flashcard, an SD card or the like, as well as any other storage referred to herein or any other storage medium referred to herein.

A computer program according to the present invention encompasses a program code by which a conventional control device of a blood treatment apparatus is programmed to be a control device according to the present invention, when the computer program runs on a computer.

It will be appreciated that the execution of the various machine-implemented processes and steps described herein may occur via the execution, by one or more respective processors, of processor-executable instructions stored on one or more tangible, non-transitory computer-readable mediums (such as random access memory (RAM), read-only memory (ROM), programmable read-only memory (PROM), and/or another electronic memory mechanism). Thus, for example, operations performed by a control device or a blood treatment apparatus as discussed herein may be carried out according to instructions stored on and/or applications installed on one or more respective computing devices.

Embodiments according to the present invention may comprise one or more of the following features in any combination, unless the person skilled in the art recognizes their combination as technically impossible. Advantageous developments of the present invention are each also subject-matter of the dependent claims and embodiments.

In all of the statements made herein, the use of the expression "may be" or "may have" and so on, is to be understood synonymously with "preferably is" or "preferably has," and so on respectively, and is intended to illustrate embodiments according to the present invention.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" (also "a/an") as encompassing "at least one". This understanding is also equally encompassed by the present invention as the interpretation that a numeric word, for example, "one" (also "a/an") may alternatively mean "exactly one", wherever this is evidently technically possible for the person skilled in the art. Both understandings are encompassed by the present invention and apply herein to all used numerical words.

Whenever reference is made herein to spatial indications, such as "top", "bottom", "left" or "right", the skilled person understands this to mean the arrangement in the figures attached herein and/or in the state of use. "Below" is closer to the center of the earth or the lower edge of the figure than "above".

Whenever an embodiment is mentioned herein, it is then an exemplary embodiment according to the present invention.

When it is disclosed herein that the subject-matter according to the present invention comprises one or several features in a certain embodiment, it is also respectively disclosed herein that the subject-matter according to the present invention does, in other embodiments, likewise according to the present invention, explicitly not comprise this or these features, for example, in the sense of a disclaimer. Therefore, for every embodiment mentioned herein it applies that the converse embodiment, e.g. formulated as negation, is also disclosed.

If method steps are mentioned herein, the device according to the present invention is in some embodiments configured to execute one, several or all of these method steps—in particular if said steps are ones that can be carried out automatically—in any combination or to control corresponding devices which names are respectively based on the designation of the corresponding method step (e.g. "to determine" as a method step and "determining device" for the device, etc.) and which devices may also be part of the apparatus(es) according to the present invention or connected thereto in signal communication.

Whenever programed or configured is mentioned herein, then these terms may in some embodiments be interchangeable.

When reference is made herein to a signal communication or communication connection between two components, this may be understood to mean a connection that exists in use. Likewise, it may be understood herein that there is a preparation for such a signal communication (wired, wireless, or otherwise implemented), for example, by a coupling of both components, such as by pairing, etc.

Pairing is to be understood as a process that takes place in connection with computer networks in order to establish an initial link between computer units for the purpose of communication. An example of this is the establishment of a Bluetooth connection, by which various devices (e.g. smartphone, headphones) are connected to one another. Pairing is sometimes referred to as bonding.

When method steps are mentioned herein, it is then provided, in some embodiments, that said method steps are to occur before or after a treatment of the patient, for instance while the patient is not connected to the apparatus, via e.g. the extracorporeal blood circuit or the like, or that a treatment has not yet begun or is already completed.

The control device may prompt the execution of all or substantially all of the method steps. The method according to the present invention may be carried out essentially or completely by the control device. It may be partially carried out by the control device, in particular those steps which do not require or relate to human intervention and/or initialization may be carried out by the control device. The control device may serve purely as a control device or also as a closed-loop control device.

In several embodiments, the control device is present in or on the blood treatment apparatus, for instance together with other components or devices of the blood treatment apparatus in a common housing of the blood treatment apparatus.

In some embodiments of the control device according to the present invention, the first data and/or the second data is or encompasses scripts, series of scripts, encodings regarding which scripts are to be executed, durations of how long a script is to be executed, applications, instruction lists, prescriptions, parameters with which the scripts are to be executed, and/or status information.

The parameters, with which to execute the scripts, may encompass for example duration, blood pump rate, type of anticoagulation (heparin, citrate-calcium), dialysate flow rate, substitute fluid rate, ultrafiltration (UF) profile number, etc.

Status information may, for example, encompass information about the current treatment or the patient's condition. Likewise, current values of both the patient and the machine, values about the course of treatment and/or machine parameters may be encompassed in the status information. In this, machine parameters may be present as raw data and/or be processed.

The execution of scripts may be conditional, for example in some embodiments, the blood treatment apparatus or the control device may determine, after performing an independent check, that execution of the first data associated with the second data received from the central unit is not admissible, permitted, or possible in a blood treatment session using the blood treatment apparatus.

Time durations, i.e., how long a script is executed, may for example encompass, executing a script endlessly, i.e., until a new command comes from the central unit, for a predetermined period or until an event occurs at the blood treatment apparatus.

In certain embodiments of the present invention, in particular, the second data is information about which first data, i.e., for example, which of the sequences of control commands or regulation commands, is required for a function of the blood treatment apparatus.

In further embodiments of the present invention, in particular, the second data encompasses instructions and/or information about the order in which the respective associated first data, i.e., for example the order of the sequences of control commands or regulation commands, are used as treatment data to control and/or regulate the blood treatment (apparatus).

When "instruction lists" are mentioned here, this does not mean instruction lists, as defined in the international standard of the International Electrotechnical Commission IEC61131-3.

Thus, instead of receiving individual instructions as in the remote procedure call, in several embodiments the control device receives entire lists of instructions that it can process in interaction with the data storage device and the blood treatment apparatus, preferably in an automated manner.

These lists with instructions may in these embodiments be second data which associated with the first data from the data storage, ultimately result in the treatment data (as scripts with suitable parameters and the like) that may be executed on the blood treatment apparatus.

In several embodiments, the control device is programmed to control the blood treatment apparatus based on at least one set of standard control data from the data storage, which is not the first or second data, and/or wherein no association of first data to second data, or vice versa, is required to control the blood treatment apparatus based on the standard control data.

The blood treatment apparatus may thus be controlled or regulated by its control device based on standard control data—e.g. also stored in the data storage—or is prepared and programmed accordingly for this purpose. Such standard data may be understood as emergency data by which the blood treatment may continuously be carried on even in the event of a data interruption between the blood treatment apparatus or its control device and the central unit, for example by manual operation using the blood treatment apparatus (touch screen, user interface, etc.).

In some embodiments, the control device comprises a user interface configured to enable a user to control or regulate the blood treatment apparatus or to intervene in the control or regulation thereof.

In several embodiments, the control device is further programmed to request or receive from the central unit update data for an update of the first data and/or standard control data stored in the data storage.

The control device may also be programmed to update the stored first data and/or the standard control data by or based on the update data and to store them again in the data storage after the update. New first data and/or new standard data may be generated in this process.

As a result, the deployment of new scripts that have been developed in the meantime may be significantly accelerated on end devices that are already being used by the end customer. Instead of rolling out firmware updates via a service network (to a service technician, for example), this is done simply and promptly by the present invention, in that new scripts in the form of second data are made available, for example on the cloud server as the central unit.

In some embodiments, the control device retrieves the update data or accepts it on receipt from the central unit according to predetermined criteria.

The predetermined criteria may be or encompass, for example, an association with a specific group, e.g., a region, an installation location, data concerning the next patient to be treated, device age, model number, current number of treatments carried out, or the like.

In this, an installation location may be determined absolutely, for example via Global Positioning System (GPS), and/or relatively, for example via a distance to other devices, chip card information or the like. In particular, the installation location may take into account linguistic and/or regulatory particularities or customs prevailing, for example, at the installation location, as provided in certain embodiments.

In certain embodiments, a predetermined criterion may alternatively or additionally be or encompass the quality of the Internet connection, for example as the average transmission rate.

In several embodiments, the update data encompasses a command or routine for activating/unlocking data, optionally first data in the data storage.

In some embodiments, the update data encompasses a command to provide additional data for use in a treatment session with no connection to the central unit. Advantageously, a blood treatment session may thus be subsequently carried out offline. For example, in these embodiments, a patient card with a data storage function may be used, on which update data relating to patient-specific parameters may be stored. This update data may be retrieved or read from the patient card during the patient' treatment, rather than via the Internet. In addition, in certain embodiments, changes to the data stored on the card (for at least one future offline treatment) may be stored or made after a treatment.

In several embodiments, the control device according to the present invention is further programmed to check the plausibility of the received first data and/or of second data for the control of the blood treatment apparatus prior to their use for the control of same and/or to check, e.g. via trigger elements, the admissibility of this data. Thus, in the data storage or at another suitable location to which the control device of the blood treatment apparatus has access, it can be specified which form, format, structure, etc. the second data and/or plausibility elements transmitted together with them must have in order to be able to recognize the validity of the transmitted second data. For example, for the plausibility check, it may be stored that the second data must encompass certain trigger elements, that certain first data must always be associable to the second data, while other data must not be associable, or must not associable in specific combinations or sequences, in which the processes represented by the first data should take place on the blood treatment apparatus during a treatment, and so on. For example, in a situation where the second data provides a treatment configuration, but the treatment duration is not defined by the data, the second data may fail the plausibility check.

Checking the logic or the admissibility of the structure of the first and/or second data, or prompting such a check to be performed may be provided in certain embodiments. Such a check may also be provided on the blood treatment apparatus in certain embodiments. For example, checking for admissibility of the data may include checking for possible functions of the device and whether the functions of the device are sufficient with regard to the control operations instructed according to the second data. For example, in case the second data passes the plausibility check but indicates a treatment that the device is not capable of providing (e.g., prescribing hemodiafiltration for a device not capable of hemodiafiltration), the second data may then fail the admissibility check.

In some embodiments, the control device is programmed to actively request new first data from the data storage and/or new second data from the central or external unit, in response to a negative result of the plausibility or admissibility check. The new first data may, in several embodiments, replace previously transmitted first data that was not recognized as plausible or admissible, and proceed with the new first data as generally described herein for first data.

In some embodiments, the control device is programmed to accordingly notify the central unit in the case of a predetermined events, which usually occur in the course of the actions of the blood treatment apparatus which are encoded by the first data. The central unit may be programmed to receive such notifications, analyze them and, if necessary, actively send new second data to the control device which in turn continues the treatment using the new first data which it may associate with the new second data.

Alternatively or additionally, a notification may be sent to third parties, for example via a further device with display unit, e.g. a mobile phone of the nursing staff. In these embodiments, it may be provided that after these third parties have analyzed the displayed notifications, the control device receives new second data or first data which has been actively transmitted by the third parties. The control device may then, in turn, continue the treatment using new first data or second data.

For example, in the event of an alarm (such as a venous pressure alarm), the control device may contact the external or central unit, and the blood treatment apparatus can remain in an alarm state, i.e. a safe device state, intended for such an alarm event until a response is received. The central unit could then respond with new second data (instruction/ prescription sequence), e.g. "start UF program at rate xy to depressurize", after successful depressurization, further exchange of second data with the central unit would then be possible but not necessary (e.g. "then run a test sequence (record pressure increase while blood pump rate continu- ously increases", "send results back to the central unit" (including status information whether pressure alarm still exists)). Upon completion of a measurement cycle or test cycle, the control device could request new instructions from the central unit and/or transmit status information to the central unit. In certain embodiments, it may be provided to transmit status information periodically (always). The central unit may respond with another script, as further second data, e.g. to continue the treatment using associated first data.

In this example, if there is no response from the central unit within a predefined time window or if the alarm condition persists, an audible and/or visual alarm may be triggered, for example, to alert a user, in particular hospital staff such as a nurse or a doctor.

In the absence of a response from the central unit after a predefined time window, it may in some embodiments be additionally possible for the control device to execute a stored general (non-individualized) response script instruc- tion, the security of which is guaranteed by the system.

In some embodiments, if the transmission to the central unit, for example the cloud, is disrupted, it may be provided that predetermined status information that should be trans- mitted to the central unit is temporarily stored in the data storage and then transmitted collectively when a connection is or has been re-established. Status information herein may be any measured/calculated treatment parameters and device parameters, particularly those suitable for generating clinical protocols (including treatment quality, treatment duration, prescription, etc.), device protocols (among others pres- sures, flows, voltages, etc.), and/or protocols relevant for insurances (among others patient data, nursing staff data, clinic, etc.).

In some embodiments, the control device may be pro- grammed to distinguish between relevant data of long-term interest, which is to be stored and preferably to be held available again for further treatments, and data which is relevant only for a short time and thus not to be stored, in particular according to predetermined criteria. In several embodiments, the data stored on the basis of this distinction may advantageously be used to aggregate necessary data, for example for further operation of the blood treatment appa- ratus, in the event of a poor or unavailable data connection.

In several embodiments, the control device may be pro- grammed to encrypt or decrypt the first data and/or the second data. It may be alternatively or additionally provided in several embodiments that the control device is pro- grammed to authenticate and/or verify a sender of received data and/or the addressee of sent data. This serves in particular to ensure that no corrupt or manipulated data can be used. Cybersecurity technology may be used for this purpose.

In some embodiments, the blood treatment apparatus is embodied as a dialysis apparatus, hemodialysis apparatus, hemofiltration apparatus or hemodiafiltration apparatus, in particular as an apparatus for the acute renal replacement therapy, the chronic renal replacement therapy or for the continuous renal replacement therapy (CRRT).

Whenever a suitability or method step is mentioned herein, the present invention also encompasses correspond- ing programming or configuration of a suitable device or section thereof.

Some or all of the embodiments according to the present invention may have one, several, or all of the advantages mentioned above and/or in the following.

Since edge computing is often used by and with the present invention, which places lower demands on the bandwidth of the network connection used, costs for the network and/or cloud may advantageously be saved due to the lower data volume and the lower real-time requirements for the network connection.

One advantage of the present invention may be that the deployment of new scripts, developed in the meantime, on end devices already in use by the end customer may be significantly accelerated. Instead of rolling out firmware updates via a service network (to e.g. a service technician), this is advantageously done simply and promptly by the present invention, in that new scripts are made available in the form of second data for example on the cloud server as the central unit. This advantageously helps to save time and costs.

Another advantage of the present invention may be that during a trial and/or test phase (clinical trial), special scripts for data acquisition may be implemented temporarily on a data storage (edge), which may then advantageously be used to evaluate the test phases. This may also help to save costs and time.

By using the present invention, regional adaptations may advantageously be automatically detected by the end device, the data storage (edge) or the cloud. The software deploy- ment may be automatically adapted for these cases in the form of stored standard rules (settings). Advantageously, a different level of abstraction of the first and/or second data may be used as the basis for applicable law (e.g., data protection regulation, etc.) and, therefore, regional data protection laws are made easier to comply with.

For example, depending on the installation location of the blood treatment apparatus, a specific regional implementa- tion of a data protection regulation may apply. If the apparatus happens to be located in this certain region, then e.g. the transmission of personal data may require prior de-identification, anonymization, encryption and/or the like. The technical implementation of this requirement may then advantageously be carried out, for example without human intervention, by software update directly on the blood treat- ment apparatus. It is further advantageously possible by the present invention to adapt e.g. linguistic displays and/or outputs relating to new functions to the language of the location country.

Another advantage of the present invention may be that additional data regarding enhanced user guidance may be transferred from the central unit to the control device of the blood treatment apparatus. This may be particularly relevant in domestic applications. In such cases, it may be deter- mined by the present invention, for example, that the loca- tion of the treatment apparatus is outside of a clinic, e.g. because the distance to further blood treatment apparatus exceeds a predetermined value.

A further advantage of the present invention may be that the interface between the blood treatment apparatus or the control device according to the present invention and the local or global network now also complies with stricter regulations and requirements, including those from the field of cybersecurity. Attack surfaces/vectors on the blood treatment apparatus are advantageously kept small in order to keep the possibility of manipulation of the blood treatment apparatus, in particular by outside third parties, as low as possible.

All the advantages achievable with methods according to the present invention may in certain embodiments according to the present invention also be achieved undiminished with devices according to the present invention, and vice versa.

FIG. 1 shows, schematically simplified, a control device 150 according to the present invention for a blood treatment device 100 in a system 1000 according to the present invention in a first embodiment, wherein the control device 150 may serve to control or regulate.

In this embodiment, the control device 150 is programmed to be in signal communication with a data storage 500. In FIG. 1, double arrows indicate that, and where, a signal communication is provided/programmed/established for unidirectional or bidirectional transfer of data, such as for transfer of the first data D1 between control device 150 and data storage 500.

The data storage 500 is shown as a separate device in the example of FIG. 1; this is not to be understood as limiting. The data storage 500 may alternatively be part of the control device 150, of the blood treatment apparatus 100, etc. However, the data storage 500 is provided, or prepared, to be in signal communication with the control device 150, at least during operation of the control device 150.

The control device 150 is further programmed to control or regulate the blood treatment apparatus 100 for the treatment a patient or for treating a patient. This may be done based on a plurality of sequences of control or regulating commands contained in the first data D1, after the first data D1 has been transmitted to the control device 150 from the data storage 500.

Further, the control device 150 is optionally programmed to be in signal communication with a central unit ZE, such as a cloud or network, shown in the figures by a cloud. The central unit may also be referred to as an external entity which is external relative to the control device, the data storage, and the blood treatment apparatus. This signal communication is provided/programmed/suitable for unidirectional or bidirectional transfer of second data D2 and is therefore also shown by a double arrow in FIG. 1.

The control device 150 is programmed to receive and/or retrieve second data D2 from the central unit ZE. The second data D2, thus received or retrieved, is associated with first data D1 from the data storage 500 by the control device 150, according to predetermined rules which are recorded or registered for example in a table, and said first data D1 is loaded from the data storage 500. The loaded first data D1 is used in an ongoing or upcoming, e.g. planned, blood treatment session, in particular to control or regulate the operation of the blood treatment apparatus 100 in this blood treatment session. In these embodiments, the control device 150 has thus determined and/or generated treatment data BD based on the second data D2 received from the central unit ZE and on the association made with the first data D1, which may, or should, subsequently serve as control data for the blood treatment apparatus 100.

The first data D1, the second data D2 and/or the treatment data BD may be or may encompass scripts, series of scripts, encodings of which scripts are to be executed, how long a script is to be executed, applications, instruction lists, prescriptions, parameters with which the scripts are to be executed and/or status information.

Parameters with which the scripts are to be executed may be or may encompass, for example, an indication of or information about a duration, a blood pump rate, a dialysate flow rate, a substitution rate, a UF profile number, or the like.

Status information may be or encompass information about the current treatment, about a condition of the patient, and/or about the course of treatment. Alternatively, it may be or encompass current values, both of a human and of the apparatus, and/or machine parameters. It is irrelevant whether the system information is available as raw data or already further processed.

In several embodiments, the control device 150 may be programmed to check the plausibility of the received first data D1 or second data D2 for controlling the blood treatment apparatus 100 before using it for controlling same. Alternatively or additionally, the admissibility of the first data D1 or second data D2 may be checked using trigger elements.

The control device 150 and the data storage 500 are shown in FIG. 1 as separate components of the system 1000. In certain embodiments, they may be comprised by the blood treatment apparatus 100 and/or provided in a common housing; this is indicated in FIG. 1 by a dashed line.

In some embodiments it may be provided that at least one set of standard control data is stored in the data storage 500, by which data the control device 150 is able to regulate or control the blood treatment apparatus 100, in particular autonomously. The standard control data may be neither first data D1 nor second data D2. Alternatively or additionally, there is no need to associate first data D1 with second data D2, or vice versa, to control or regulate the blood treatment apparatus 100 based on the standard control data. In alternative embodiments, the standard control data may also be a local copy of second data D2, which may be associated with the first data D1 in the event that no connection to the central unit ZE can be established, wherein the first data D1 associated in this way may be used to control and/or regulate the blood treatment (apparatus).

Figure 1A:
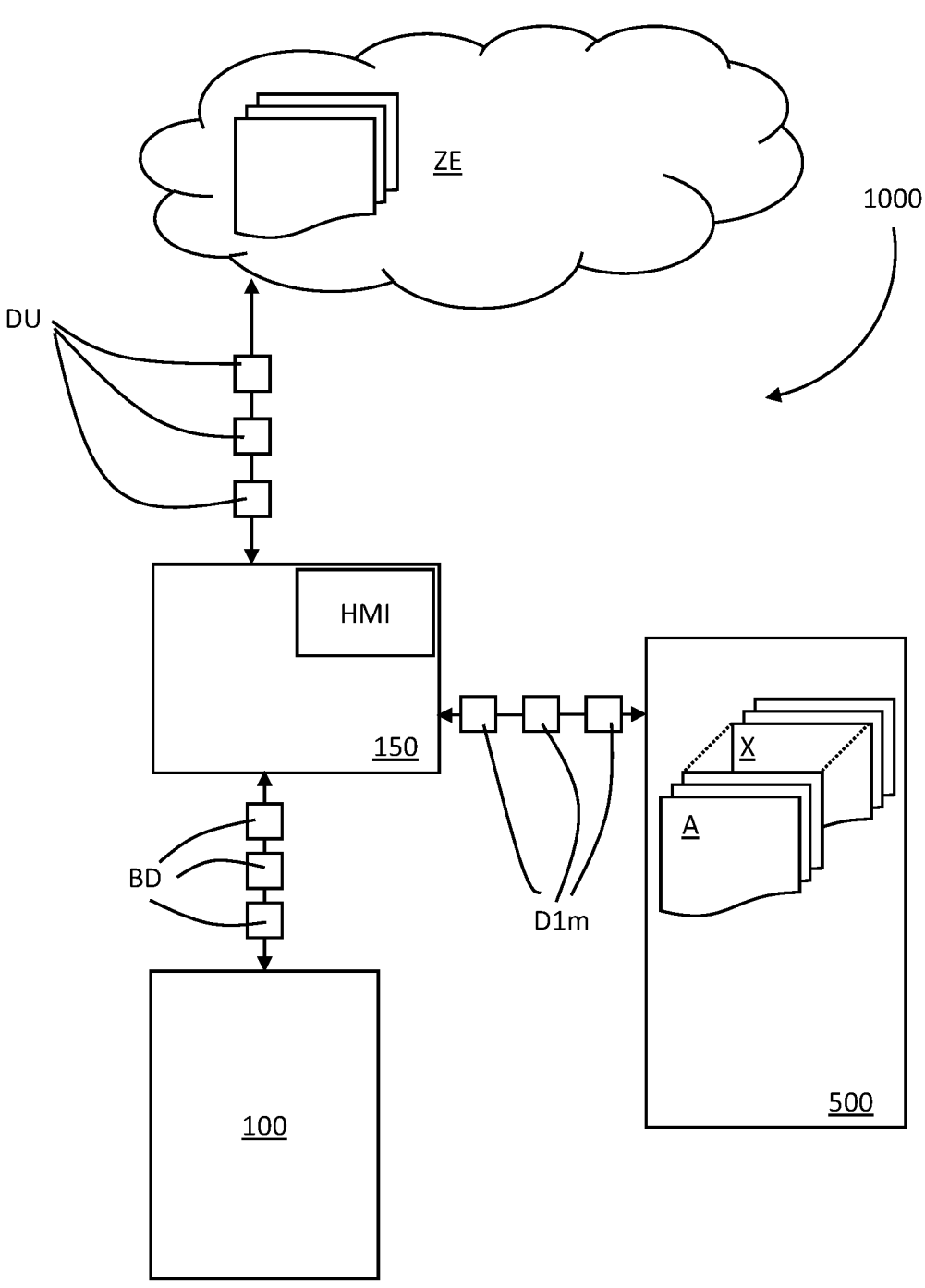
FIG. 1a shows, schematically simplified, a control device according to the present invention for a blood treatment apparatus in a system according to the present invention, in an exemplary embodiment.

FIG. 1a shows, schematically simplified, a control device 150 according to the present invention for a blood treatment apparatus 100 of a system 1000 according to the present invention in a second embodiment.

In order to avoid repetition, reference is made to the statements on FIG. 1, which may also apply here, and only the differences from or to FIG. 1 are discussed below.

Alternatively or additionally, the control device 150 may comprise a user interface HMI being configured to enable a user to control or regulate the blood treatment apparatus, prompt the blood treatment apparatus 100 to be regulated or controlled or to intervene in the control or regulation thereof.

The control device 150 may be programmed to query the central unit ZE for update data DU for the first data D1 and/or the standard control data stored in the data storage 500.

Alternatively or in addition, the control device 150 may be programmed to receive update data DU for the first data D1 and/or standard control data stored in the data storage 500 from the central unit ZE.

The control device 150 is optionally programmed to modify the first data D1 and/or the standard control data stored in the data storage 500 by the update data DU and to store it as modified data D1m.

In some embodiments, the update data DU may be specifically requested by the control device 150 according to predetermined criteria from the central unit ZE or may be accepted by the central unit ZE upon receipt. Criteria may be, for example, association with a particular group, e.g., region, installation location, which patient will be treated next, or the like.

The update data DU may encompass a command or routine for activating/unlocking data. The activated/unlocked data may depend directly or indirectly on certain criteria, which may include, amongst others, the location as described herein. Further criteria may be certain treatment modalities, equipment packages of the blood treatment apparatus (basic—advanced—executive) or the like.

Alternatively or in addition, an update may be or encompass providing additional data. This additional data may enable a subsequent treatment session to be performed without a connection to the central unit ZE, quasi offline. Advantageously, this may enable a treatment session to be reliably performed with no dependence on the presence of an available or stable or fast network connection.

Figure 2:
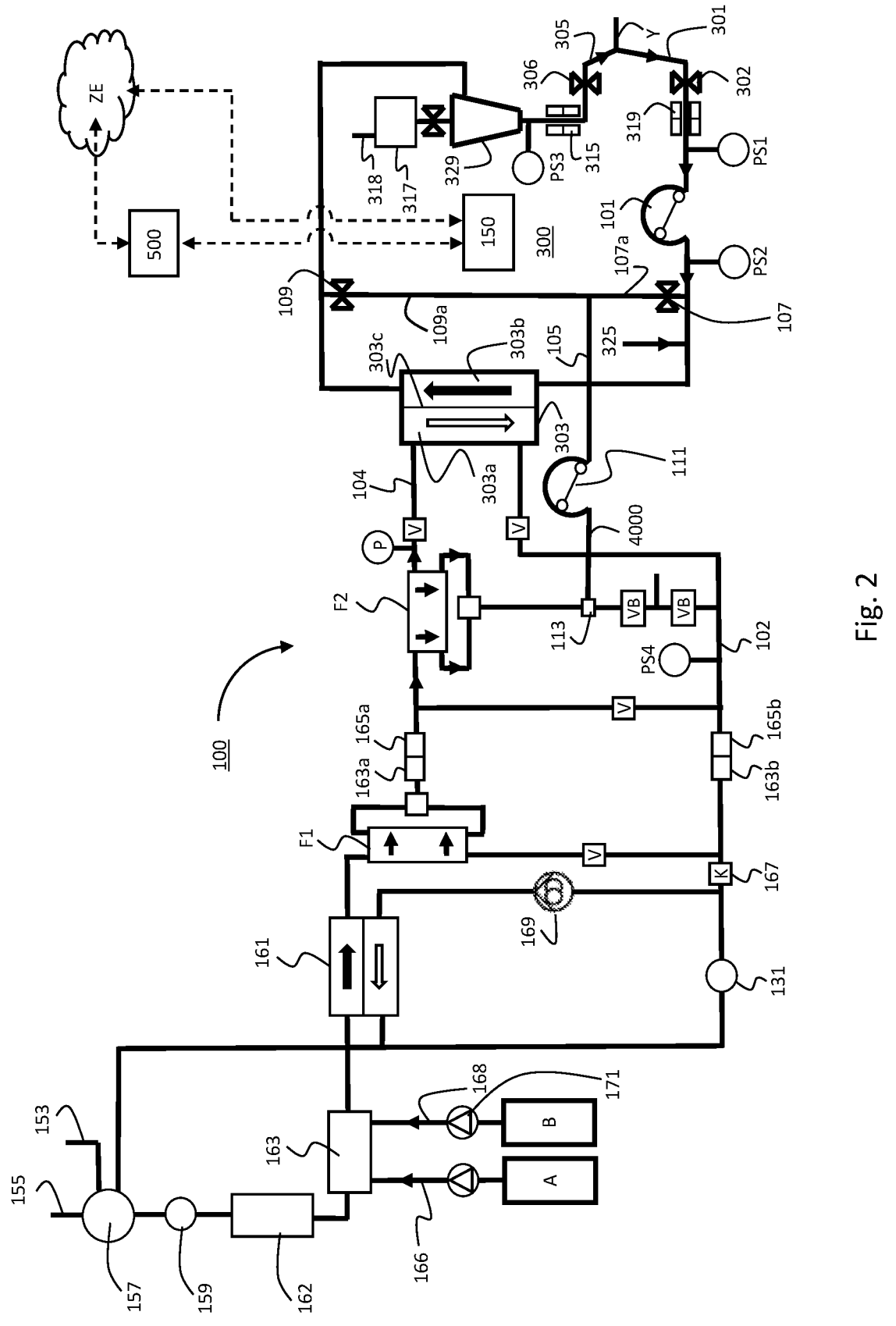
FIG. 2 shows, schematically simplified, a fluid line structure of a blood treatment apparatus according to the present invention in an exemplary embodiment.

FIG. 2 shows, schematically simplified, a fluid line structure of a blood treatment apparatus 100 according to the present invention in a first embodiment.

The blood treatment apparatus 100, which is shown in an at least partially equipped state of use, is connected to an extracorporeal blood circuit 300, which blood circuit 300 may be connected to the vascular system of the patient, not shown, for executing a treatment using double-needle access, or using e.g. an additional Y-connector (reference numeral Y), as is shown in FIG. 2 using single-needle access, and which may be optionally not included in the blood treatment apparatus 100. In other embodiments, the blood circuit 300 may, however, be part of the blood treatment apparatus 100. The blood circuit 300 may be present, in optionally sections thereof, in or on a blood cassette.

Pumps, actuators and/or valves in the area of the blood circuit 300 are connected to the blood treatment apparatus 100 according to the present invention or to a control device 150, comprised by it, in signal communication where this is necessary for controlling or regulating.

The blood circuit 300 comprises (or is connected to) an arterial patient tube clamp 302 and an arterial connection needle of an arterial section or of an arterial patient line, blood collection line or first line 301. The blood circuit 300 also comprises (or is connected to) a venous patient tube clamp 306 and a venous connection needle of a venous section, a venous patient line, a blood return line or a second line 305.

A blood pump 101 is provided in or at the first line 301, a substitute fluid pump 111 is connected to a dialysis liquid inlet line 104 for conveying fresh dialysis liquid, which is filtered in a further filter stage (F2) (substitute fluid). A substitute fluid line 105 may be fluidically connected to the inlet line 104. Using the substitute fluid pump 111, substitute fluid may be introduced by predilution, via a predilution valve 107, or by postdilution, via a postdilution valve 109, via associated lines 107a or 109a into line sections, for example into the arterial line section 301 or into the venous line section 305 (here between a blood chamber 303b of a blood filter 303 and a venous air separation chamber or venous blood chamber 329) of the blood circuit 300.

The blood filter 303 comprises the blood chamber 303b connected to the arterial line section 301 and to the venous line section 305. A dialysis liquid chamber 303a of the blood filter 303 is connected to the dialysis liquid inlet line 104 leading to the dialysis liquid chamber 303a and to a dialysate outlet line 102, which guides dialysate, i.e. spent dialysis liquid, leading away from the dialysis liquid chamber 303a. Suitable connectors, which may connected to each other, in particular releasably, disposed on the dialysis liquid inlet line 104 or on the dialysate outlet line 102 on the one hand and on the dialysate port on the other hand, serve for this purpose.

Dialysis liquid chamber 303a and blood chamber 303b are separated from each other by a mostly semi-permeable membrane 303c. It represents the separating borderline between the blood side with the extracorporeal blood circuit 300 and the machine side with the dialysis liquid or dialysate circuit, which is shown in FIG. 2 to the left of the membrane 303c.

The arrangement of FIG. 2 further comprises a valve V disposed in the dialysis liquid inlet line 104 upstream of the dialysis liquid chamber 303a, but downstream of a pressure sensor P. It further comprises a valve V disposed in the dialysate outlet line 102, downstream of the dialysis liquid chamber 303a, but upstream of a pressure sensor PS4.

The arrangement in FIG. 2 comprises an optional detector 315 for detecting air and/or blood. The arrangement of FIG. 2 further comprises one or two pressure sensors PS1 (upstream of the blood pump 101) and PS2 (downstream of the blood pump 101, it measures the pressure upstream of the blood filter 303 ("pre-hemofilter")) at the points shown in FIG. 2. Further pressure sensors may be provided, e.g. pressure sensor PS3 downstream of the venous blood chamber 329.

An optional single-needle chamber 317 is used in FIG. 2 as a buffer and/or compensating reservoir in a single-needle procedure in which the patient is connected to the extracorporeal blood circuit 300 using only one of the two blood lines 301, 305.

The arrangement of FIG. 2 also comprises an optional detector 319 for detecting air bubbles and/or blood.

An optional Heparin addition site 325 may be provided.

On the left in FIG. 2, a mixing device 163 is shown, which provides a predetermined mixture for the respective solution from the containers A (for A concentrate via concentrate supply 166) and B (for B concentrate via concentrate supply 168) for use by the blood treatment apparatus 100. The solution contains water from the water source 155 (on-line, e.g. as reverse osmosis water or from bags), wherein the water is heated e.g. in the heating device 162.

A pump 171, which can be referred to as concentrate pump or sodium pump, is fluidly connected to the mixing device 163 and a source of sodium, for example the container A, and/or coveys out of it. An optional pump 171, which is assigned to container B, for example for bicarbonate, can be seen.

Furthermore, FIG. 2 shows an outlet 153 for the effluent. An optional heat exchanger 157 and a first flow pump 159, which is suitable for degassing, complete the arrangement shown.

The pressure sensor PS4 may be provided downstream of the blood filter 303 on the water side, but preferably upstream of the ultrafiltration pump 131 in the dialysate outlet line 102 for measuring the filtrate pressure or membrane pressure of the blood filter 303.

Blood leaving the blood filter 303 flows through an optional venous blood chamber 329, which may comprise a deaeration device 318 and may be in fluid communication with the pressure sensor PS3.

The exemplary arrangement shown in FIG. 2 comprises the control device 150 according to the present invention. It may be in a wired or wireless signal communication with any of the components mentioned herein—especially or in particular with the blood pump 101—to control or regulate the treatment apparatus 100

Furthermore, the control device 150 is in wired or wireless signal communication (shown generally as dashed lines in FIG. 2) with the data storage 500 for retrieving or transmitting first or second data D1, D2. The data storage 500 may in turn be in signal communication with a central unit ZE, here exemplarily a cloud. The central unit ZE may alternatively or additionally be in direct signal communication with the control device 150.

By using the device for on-line mixing of the dialysis liquid, a variation of its sodium content, controlled by the control device 150, is possible within certain limits. For this purpose, in particular the measured values determined by the conductivity sensors 163*a*, 163*b* may be taken into account. Should an adjustment of the sodium content of the dialysis liquid (sodium concentration) or of the substitute fluid turn out to be necessary or desired, this can be done by adjusting the conveyance rate of the sodium pump 171.

In addition, the blood treatment apparatus 100 comprises means for conveying fresh dialysis liquid and dialysate. A first valve may be provided between the first flow pump 159 and the blood filter 303, which first valve opens or closes the inflow towards the blood filter 303 at the inlet side. A second, optional flow pump 169 which conveys dialysate through the drainage line 153 is provided e.g. downstream of the blood filter 303. A second valve may be provided between the blood filter 303 and the second flow pump 169 at the outlet side, which second valve opens or closes the outflow.

Furthermore, the blood treatment apparatus 100 optionally comprises a device 161 for balancing the flow flowing into and out of the dialyzer 303 on the machine side. The device 161 for balancing is preferably arranged in a line section between the first flow pump 159 and the second flow pump 169.

The blood treatment apparatus 100 further comprises means, such as the ultrafiltration pump 131, for the precise removal of a volume of liquid, as predetermined by the user and/or by the control device 150, from the balanced circuit.

Sensors such as the optional conductivity sensors 163*a*, 163*b* serve to determine the conductivity, which in some embodiments is temperature-compensated, as well as the fluid flow upstream and downstream of the dialyzer 303.

Temperature sensors 165*a*, 165*b* may be provided as one or a plurality thereof. Temperature values supplied by them may be used to determine a temperature-compensated conductivity.

An optional compressed air source, e.g. a compressor, may be provided on the machine side upstream of the blood filter 303.

A leakage sensor 167 is optionally provided. It may be provided at or in port 100.

Further flow pumps in addition or alternatively to e.g. the one with the reference numeral 169 may also be provided.

A number of optional valves are each denoted with V in FIG. 2; by-pass valves with VB.

In some embodiments, the control device 150 determines the electrolyte and/or liquid balance based on the measured values of the aforementioned optional sensors.

Filters F1 and F2 can be provided connected in series.

Even when using non-pure water, the filter F1 exemplarily serves here to generate sufficiently pure dialysis liquid by the mixing device 163, which then flows through the blood filter 303, e.g. using the countercurrent principle.

The filter F2 exemplarily serves herein to generate sterile or sufficiently filtered substituate from the sufficiently pure dialysis liquid leaving the first filter F1, by filtering e.g. pyrogenic substances. This substitute fluid may then be safely added to the extracorporeally flowing blood of the patient and thus ultimately to the patient's body.

The blood treatment apparatus 100 is optionally shown in FIG. 2 as a device for hemo(dia)filtration. However, hemodialysis apparatuses are also covered by the present invention, although not specifically represented in a figure.

The arrow shown in FIG. 2 generally indicate the flow direction in FIG. 2.

Figure 3:
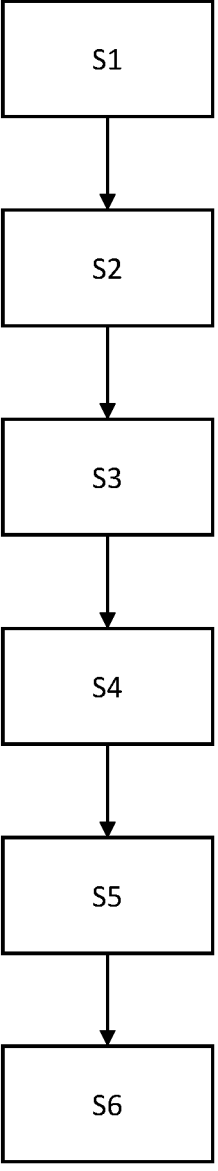
FIG. 3 shows, schematically simplified, a course of a method according to the present invention in an exemplary embodiment.

FIG. 3 shows, schematically simplified, a course of the method according to the present invention in an exemplary embodiment.

Reference is made to the reference numerals in FIG. 1 to FIG. 1*a*.

Here, step S1 represents a providing a system according to the present invention.

In step S2, second data D2 is received from or by a central unit ZE not present on or in the blood treatment apparatus 100, for example a cloud or a network. This second data may be temporarily stored, for example, in the data storage 500.

As a further step S3, the method comprises associating first data D1 with the received second data D2 according to predetermined rules, for example from a table.

In some embodiments, associating the first data D1 with the second data D2 generates new data, this is the treatment data BD, which reflect the result of the association.

In step S4 of the method according to the present invention, the first data D1 and/or treatment data BD is transferred to the control device 150 from a data storage 500, which is preferably present in or on the blood treatment apparatus 100.

In step S5, the control device 150 determines the associated first data D1 and/or the treatment data BD as control data for an ongoing or upcoming, e.g. planned, blood treatment session on the basis of the second data D2 and the association made with the first data D1.

Based on this determined associated first data D1 and/or the treatment data BD, the operation of the blood treatment apparatus 100 in the ongoing or upcoming blood treatment session is then controlled or regulated by the control device 150 in step S6.

The present invention is not limited to the above-described embodiments, which serve merely for illustrative purposes and as examples.

The following example is intended to illustrate one embodiment of the method according to the invention.

A trigger element order/recipe/sequence, for example, consisting of the string "AAX CBADD XF," is sent as second data D2 from a central unit ZE, here a cloud, to a control device 150 according to the present invention. The control device 150 recognizes the start pattern AA as a valid pattern of a sequence of elements to be carried out. In the element X announcing a sequence of scripts, the control device 150 recognizes the subsequent sequence CBADD as a sequence of scripts to be executed. The announcing element X with F validly completes the sequence of elements. The sequence of scripts CBADD to be carried out is feasible according to the plausibility rules, therefore these scripts are assigned as a first data D1 and, in interaction with the data storage 500, on which the first data D1 is stored, is transmitted as a sequence of scripts, for example as treatment data BD and/or associated data, to the control device 150 so that, by using the control device 150, the corresponding blood treatment session may be performed using the blood treatment apparatus 100. After completion of the blood treatment session, the central unit ZE could be informed about the performed (successful) execution, for example by a mirrored trigger sequence XF DDABC AAX (optionally, or only by a hash value confirming the executed scripts).

It will be appreciated that the first data D1 may be locally stored on the device and may be configured for basic control of the device parts. The first data D1 may thus, for example, be limited to only the basic functions of the device parts while not providing a treatment configuration. For performing a treatment, the device may be dependent on external input, such as second data D2. This second data D2, which may be, for example, obtained from the cloud, instructs the device as to how to line up its basic parts and the first data D1 into a sequence that corresponds to a treatment to be performed. Thus, for example, the first data D1 may correspond to controlling electrical/mechanical parts of the device, and the second data D2 may correspond to a medical therapy and/or patient information.

In some exemplary implementations, as discussed above, the device may include standard control data for carrying out certain treatments. In other exemplary implementations, the device may be dependent on the second data D2 to carry out any type of treatment.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A system, comprising:
A data storage configured to store a plurality of scripts;
A blood treatment apparatus configured to provide a blood treatment session;
A control device; and
A central cloud computing device configured to send a communication comprising a sequence of scripts to the control device;
Wherein the data storage is part of the blood treatment apparatus and/or the control device; and
Wherein the control device is configured to:

receive the sequence of scripts from the central cloud computing device;
After receiving the sequence of scripts, control the blood treatment apparatus using scripts of the plurality of scripts executed according to the received sequence of scripts; and
After completion of the blood treatment session, inform the central cloud computing device regarding successful execution of the sequence of scripts, wherein informing the central cloud computing device regarding the successful execution of the sequence of scripts is based on providing a mirrored sequence.

2. The system according to claim 1, wherein the communication further comprises information regarding how long a respective script is to be executed.

3. The system according to claim 1, wherein the control device is further configured to control the blood treatment apparatus based on standard control data from the data storage.

4. The system according to claim 3, wherein the control device comprises a user interface configured to:
enable a user to control, regulate, or prompt the blood treatment apparatus to be regulated or controlled; or
enable a user to intervene in the control or regulation of the blood treatment apparatus.

5. The system according to claim 3, wherein the control device is further configured to:
receive update data from the central cloud computing device for updating the plurality of scripts and/or the standard control data stored in the data storage; and
update the plurality of scripts and/or the standard control data using the update data.

6. The system according to claim 5, wherein the control device is further configured to:
request the update data from the central cloud computing device.

7. The system according to claim 5, wherein the update data comprises a command or routine for activating or unlocking data.

8. The system according to claim 5, wherein the update data comprises a command for providing additional data for use in a treatment session without connection to the central cloud computing device.

9. The system according to claim 1, wherein the control device is further configured to:
check plausibility of the sequence of scripts according to plausibility rules before using the sequence of scripts for controlling the blood treatment apparatus.

10. The system according to claim 9, wherein the control device is further configured to:
request new data from the central cloud computing device based on the plausibility check having a negative result.

11. The system according to claim 1, wherein the blood treatment apparatus comprises the control device.

12. The system according to claim 1, wherein the blood treatment apparatus is connected to the control device.

13. The system according to claim 1, wherein the blood treatment apparatus comprises a dialysis apparatus, a hemodialysis apparatus, a hemofiltration apparatus, or a hemodiafiltration apparatus.

14. A method for controlling a blood treatment apparatus, comprising:
Storing, by a data storage, a plurality of scripts;
Receiving, by a control device, the plurality of scripts from the data storage, wherein the data storage is part of the blood treatment apparatus and/or the control device;

Receiving, by the control device, a communication comprising a sequence of scripts from a central cloud computing device;

After receiving the sequence of scripts, controlling, by the control device, the blood treatment apparatus to provide a blood treatment session using scripts of the plurality of scripts executed according to the received sequence of scripts; and After completion of the blood treatment session, informing, by the control device, the central cloud computing device regarding successful execution of the sequence of scripts, wherein informing the central cloud computing device regarding the successful execution of the sequence of scripts is based on providing a mirrored sequence.

15. A non-transitory computer-readable medium having processor-executable instructions stored thereon for controlling a blood treatment apparatus, wherein the processor-executable instructions, when executed, facilitate performance of the following:

Receiving, by a control device, a plurality of scripts from a data storage, wherein the data storage is part of the blood treatment apparatus and/or the control device;

Receiving, by the control device, a communication comprising a sequence of scripts from a central cloud computing device;

After receiving the sequence of scripts, controlling, by the control device, the blood treatment apparatus to provide a blood treatment session using scripts of the plurality of scripts executed according to the received sequence of scripts; and After completion of the blood treatment session, informing, by the control device, the central cloud computing device regarding successful execution of the sequence of scripts, wherein informing the central cloud computing device regarding the successful execution of the sequence of scripts is based on providing a mirrored sequence.

16. The system according to claim 1, wherein the communication from the central cloud computing device to the control device further comprises a start pattern; and wherein the control device is configured to recognize whether the start pattern is a valid start pattern.

17. The system according to claim 16, wherein the communication from the central cloud computing device to the control device further comprises an announcing element.

* * * * *